United States Patent [19]

Suh

[11] Patent Number: 4,764,168
[45] Date of Patent: Aug. 16, 1988

[54] TYMPANIC MEMBRANE IMPLANT

[76] Inventor: Ku W. Suh, 3906 Ardleigh Dr., Greenville Manor, Wilmington, Del. 19807

[21] Appl. No.: 90,840

[22] Filed: Aug. 28, 1987

[51] Int. Cl.⁴ ............................................. A61M 5/325
[52] U.S. Cl. ........................................ 604/264; 623/12
[58] Field of Search ...................... 604/264; 128/1 R; 623/66, 12

[56]  References Cited

U.S. PATENT DOCUMENTS

| 3,807,409 | 4/1974 | Paparella et al. | 604/264 |
| 3,871,380 | 3/1975 | Heros | 604/264 |
| 3,982,545 | 9/1976 | Silverstein | 604/264 |
| 4,015,607 | 4/1977 | Wright, III | 604/264 |
| 4,168,697 | 9/1979 | Cantekin | 604/264 |
| 4,174,716 | 11/1979 | Treace | 604/264 |
| 4,650,488 | 3/1987 | Bays et al. | 623/12 |

Primary Examiner—Stephen C. Pellegrino

[57] ABSTRACT

The application discloses a Tympanic Membrane Implant used for equalizing pressure and allowing drainage in patients who have fluid build-up and pressure in the middle ear. The Tympanic Membrane Implant is a rigid tube, having flanges at a critical angle to one end of the tube and a tapered portion at said end of the tube for easy surgical insertion. It can contain rigid flanges at the opposite end. The invention overcomes the problem of difficulty of insertion, an inability to retrieve rigid tubes when it is desired, and the propensity of rigid tubes to be easily rejected by the body. It also overcomes the damaging effect and production of scars by the implant on the tympanic membrane.

6 Claims, 1 Drawing Sheet

U.S. Patent    Aug. 16, 1988    4,764,168
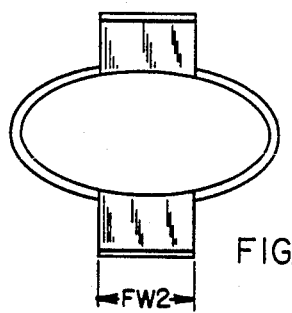
FIG. 3
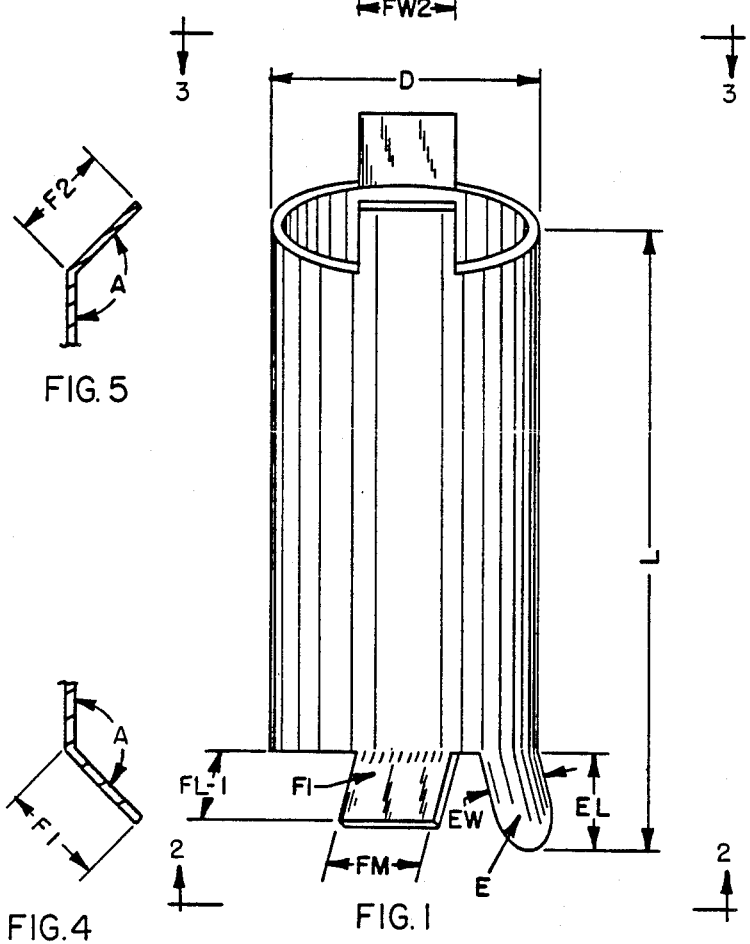
FIG. 5
FIG. 4
FIG. 1
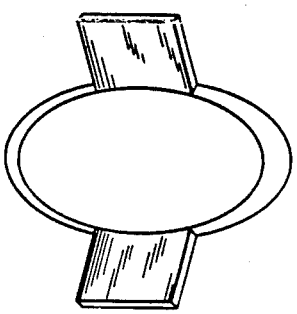
FIG. 2

TYMPANIC MEMBRANE IMPLANT

An invention in the area of medical apparatus concerned with providing a Tympanic Membrane Implant is disclosed which is also contained in application Ser. No. 819,403 filed Jan. 16, 1986 now abandoned. Filing dates are claimed for all common disclosures. The apparatus for effecting the method of this invention is also disclosed. This invention is in the area of medical apparatus and is particularly concerned with providing a Tympanic Membrane Implant, hereafter called "Implant", for surgical insertion through the tympanic membrane to stabilize pressure and allow drainage of excess fluid build-up, predominantly in children. Heretofore, there have been two approaches to the relief of pressure within the ear: durg therapy and surgery. The surgeon might insert a soft flexible tube, which tends to produce calcification, scars on the tympanic membrane and closes easily; a second choice is a rigid tube which has the advantage of less scaring and calcification effect on the tympanic membrane, but has the disadvantage, apparently due to its rigidity, of being extremely difficult to remove when removal is desired. The implant of this is designed preferably in an oval shape and it will run parallel to the fiber of the tympanic membrane and avoid damage or scar formation on the tympanic membrane.

The object of this invention is to provide a tube that has rigid strength in the tubular walls with easy insertion and yet is retained within the ear and is easily removed from the ear due to proper design of the retaining end of the tube. At the same time, the implant is designed to comply with the microscopic arrangement of the fibers of the tympanic membrane and avoid any significant damage to the tympanic membrane.

Further objects and advantages of this invention will become apparent upon reading the description of this invention and the claims describing this invention.

In the drawings:

FIG. 1 is a perspective view of the tympanic membrane implant.

FIG. 2 is a view of the tympanic membrane implant as seen along line 2—2 of FIG. 1 showing the insertion end thereof.

FIG. 3 is a view of the tympanic membrane implant as seen along line 3—3 of FIG. 1 showing the tabs which resist the implant from totally going through the eardrum.

FIG. 4 is a cross sectional view of the tabs on the insertional edge of the implant.

FIG. 5 is a cross sectional view of the tabs on the bottom edge of the implant which resists total passage through the eardrum.

With reference to FIGS. (1), (2) and (3) the hollow rigid tubular Implant is approximately 2 to 3.5 millimeters long—L. The cross sectional area of the opening of the tube is from about 1.4 square millimeters to about 2.1 square millimeters. "D", the diameter of the circle or axis of an oval, is chosen to provide the proper cross sectional area. Although the opening in the tube indicated in FIGS. (1), (2) and (3) are oval in shape, the cross sectional area of the Implant can be oval, circular or any polygonal shape, so long as the cross sectional area of said shape is within the dimensions of the area required by the invention. It is patent, however, that polygonal shapes such as rectangles or squares will not function properly, as the harsh angles will cause difficulty with the healing of the eardrum incision and the firm closing around said tube while warding off infection. Thus, the preferred shapes are oval but can be circular. The tubular body in FIG. (1) is from 2.0 to 3.5 mm long and has a protruding edge "E" known as the leading end of the Implant which allows the surgeon ease of entry through the incision and allows a minimum incision to gain access to the middle ear. EL, the length of the leading edge is from about 0.06 to about 0.5 mm and extends beyond the flanges (Item F1 FIG. 4). EW is the width of the base of E and is from about 0.2 to about 0.4 mm. An integral part of said Implant are flanges (Item F1) on the same end as EL; this is called the insertion end of said Implant. There are also shown flanges F2 (FIG. 5) on the following end, that is, the end of the implant which remains outside the tympanic membrane. F1 is soft and at least two in number and preferably not more than five in number. Said flanges are affixed to the implant at an angle "A" known as the flange fixing angle. The flange fixing angle varies from about 90 degrees to the vertical to 110 degrees to the vertical. Said angle is indicated as "A" in FIG. (1). The thickness of the implant wall varies from about 0.18 mm to about 0.30 mm, whereas the thickness of the flange is no less than 0.06 mm at the intersection of the flange and the tube wall. The thickness never exceeds 0.15 mm at the intersection. The flange length is from 0.4 mm to 1.5 mm (FL1) and the flange width (FW1) is from 0.5 to 2.0 mm. F2 flange is rigid like the tube body. F2 flanges have a width (FW2) from 1.0 mm to 2.0 mm and the flange length (FL2) from 0.5 to 1.0 mm. These flanges are designed to keep the implant from falling into the middle ear.

The F1 flange of said Implant allows the surgeon to affix the Implant within the ear and anchors the Implant. Thus, normal body motion and/or fluid pressure will not cause ejection of the Implant. The rigidty of the Implant body (2) does not allow compression or collapse of the tube after healing; that is, it keeps the surgical incision open for proper flushing action of the middle ear. All the flanges keep the Implant in proper alignment. The thinness of the intersection of the Implant's flange with the Implant body imparts great flexibility in the flange and allows, by gentle movement by a physician, extraction of the Implant from the ear with minimal difficulty and no tearing, thus assuring proper and rapid healing of the incision after its removal.

In the preferred embodiment of this invention, which is shown in FIGS. (1) through (5), the tube is oval in shape, the F1 flanges are fixed at an angle of 90–100 degrees off the vertical, i.e., angle A is 90–100 degrees and the F1 flanges are no more than 0.1 mm thick at the intersection of the flange and the tube wall and no less than 0.08 mm thick at said intersection; it then thickens rapidly, in a matter of hundredths of a mm, to the same dimension as the thickness of the tubular wall, thus assuring substance in maintaining position within the ear. The F2 flanges are rigid and at a 90 degree angle to the vertical tube wall.

The preferred embodiment has the advantages of easy insertion due to the tapered leading end of said tube, an oval shape allowing easy healing of the eardrum around the tube and minimum distortion after a straight incision. This shape, in which the F1 flanges are soft, allows the Implant to remain in the proper position and also allows easy extraction due to the bending of the flange when gentle pressure is exerted from outside the ear.

Having thus described my Invention I claim:

1. A Tympanic Membrane Implant which comprises a rigid tubular body, the cross sectional area of which is at most 2.1 square mm and no less than 1.4 mm square mm, and from about 2.0 to 3.5 mm in length and is rigid; at one end, the insertion end, of said tubular body are affixed at least two flanges which are soft and the same end has a tapered protruding edge for ease of insertion; said flanges are at an angle to the tubular body of from 90 degrees to about 110 degrees.

2. A Tympanic Membrane Implant according to claim 1 which also contains flanges at the end opposite to the insertion end, the following end, and said flanges on the following end are rigid and number from two to five.

3. A Tympanic Membrane Implant according to claim 1 where the tubular body has a wall thickness of from about 0.18 mm to 0.30 mm.

4. A Tympanic Membrane Implant acording to claim 3 where the cross sectional area is oval, the flange-tubular wall intersection on the insertion end is from 0.08 to 0.10 mm, and the overall length is at most 3.5 mm.

5. A Tympanic Membrane Implant according to claim 1 whose cross sectional area is circular or oval.

6. A Tympanic Membrane Implant according to claim 1 whose cross section is oval in shape and complys with the microscopic arrangement of fibers of the tympanic membrane, containing flexible flanges on the insertion end and rigid flanges on the following end.

* * * * *